(12) United States Patent
Vincent et al.

(10) Patent No.: US 6,193,088 B1
(45) Date of Patent: Feb. 27, 2001

(54) FLASK VENT AND METHOD OF MAKING SAME

(76) Inventors: Monty E. Vincent, 3575 Miller Rd., Ann Arbor, MI (US) 48103; John R. Costello, Jr., 3169 Cove Dr., Tecumseh, MI (US) 49286; Jonathan N. Lipsky, 587 Old Town Way, Hanover, MA (US) 02339; Ralph W. Collins, P.O. Box 435, 89 Beach St., Green Harbor, MA (US) 02041; Robert A. Giacobbe, c/o Merck & Co., Inc., P.O. Box 2000, Rahway, NJ (US) 07065

( * ) Notice: Subject to any disclaimer, the term of this patent is extended or adjusted under 35 U.S.C. 154(b) by 0 days.

(21) Appl. No.: 09/352,231

(22) Filed: Jul. 13, 1999

Related U.S. Application Data

(63) Continuation-in-part of application No. 08/606,596, filed on Feb. 26, 1996.

(51) Int. Cl.[7] .................................................. B65D 53/00
(52) U.S. Cl. ............................ 215/261; 215/6; 215/248; 215/308; 215/364; 215/DIG. 3; 220/23.8; 220/507; 220/526; 220/371
(58) Field of Search ........................ 215/6, 248, 261, 215/308, 355, 364, DIG. 3; 220/23.2, 23.8, 507, 523, 524, 526, 371, 373

(56) References Cited

U.S. PATENT DOCUMENTS

| | | |
|---|---|---|
| 2,153,981 | 4/1939 | Heineman . |
| 2,186,908 * | 1/1940 | Page et al. ............................ 215/248 |
| 2,191,447 * | 2/1940 | Beardsley ............................. 215/248 |
| 3,019,932 | 2/1962 | Singiser . |
| 3,313,712 * | 4/1967 | George ................................. 195/127 |
| 3,326,401 | 6/1967 | DeLong . |
| 3,744,661 * | 7/1973 | Fischer, Jr. ........................... 220/507 |
| 3,952,902 | 4/1976 | Prouty et al. . |
| 4,034,885 * | 7/1977 | Hunkler et al. ................. 220/507 X |
| 4,136,796 * | 1/1979 | Dubois et al. ....................... 220/256 |
| 4,235,344 * | 11/1980 | Kulle et al. .......................... 215/250 |
| 4,253,572 * | 3/1981 | Halbich ............................ 220/507 X |
| 4,271,973 * | 6/1981 | Quagliaro et al. ................... 215/308 |
| 4,935,371 * | 6/1990 | Rickloff ........................... 215/261 X |
| 5,011,018 * | 4/1991 | Keffeler ........................... 220/524 X |
| 5,037,754 * | 8/1991 | Tanaka et al. .................... 435/240.4 |
| 5,071,001 * | 12/1991 | Ryman, III ..................... 220/23.2 X |
| 5,180,073 * | 1/1993 | Fay et al. ............................. 215/261 |
| 5,188,628 * | 2/1993 | Rani et al. ....................... 215/261 X |
| 5,358,872 | 10/1994 | Mussi et al. . |
| 5,395,006 | 3/1995 | Verma . |
| 5,522,769 * | 6/1996 | DeGuiseppi ........................ 454/270 |

FOREIGN PATENT DOCUMENTS

| | | | |
|---|---|---|---|
| 265723 * | 12/1965 | (AU) .................................... 215/248 |
| 582541 * | 12/1976 | (CH) .................................... 215/248 |
| 2900807 * | 7/1979 | (DE) .................................... 215/248 |
| 0007261 * | 1/1980 | (EP) ..................................... 215/248 |
| 88/01605 * | 3/1988 | (WO) ................................... 215/248 |

* cited by examiner

Primary Examiner—Stephen K. Cronin
(74) Attorney, Agent, or Firm—Kohn & Associates

(57) ABSTRACT

A closure (20) for sealing a micro-organism container (50) is disclosed. The closure (20) includes a resilient seal (24) for sealing the container (50), a passageway (26) extending through the seal (24), or filter media (28) extending across the passageway (26) integrally molded to the seal (24) for allowing sterile gas exchange therethrough. A method of making a flask closure (20) is also disclosed. The method includes molding a sealing member (24) having a port (26) extending therethrough while simultaneously sealing a peripheral edge (31) of a filter media (28) within the passageway (26).

9 Claims, 4 Drawing Sheets

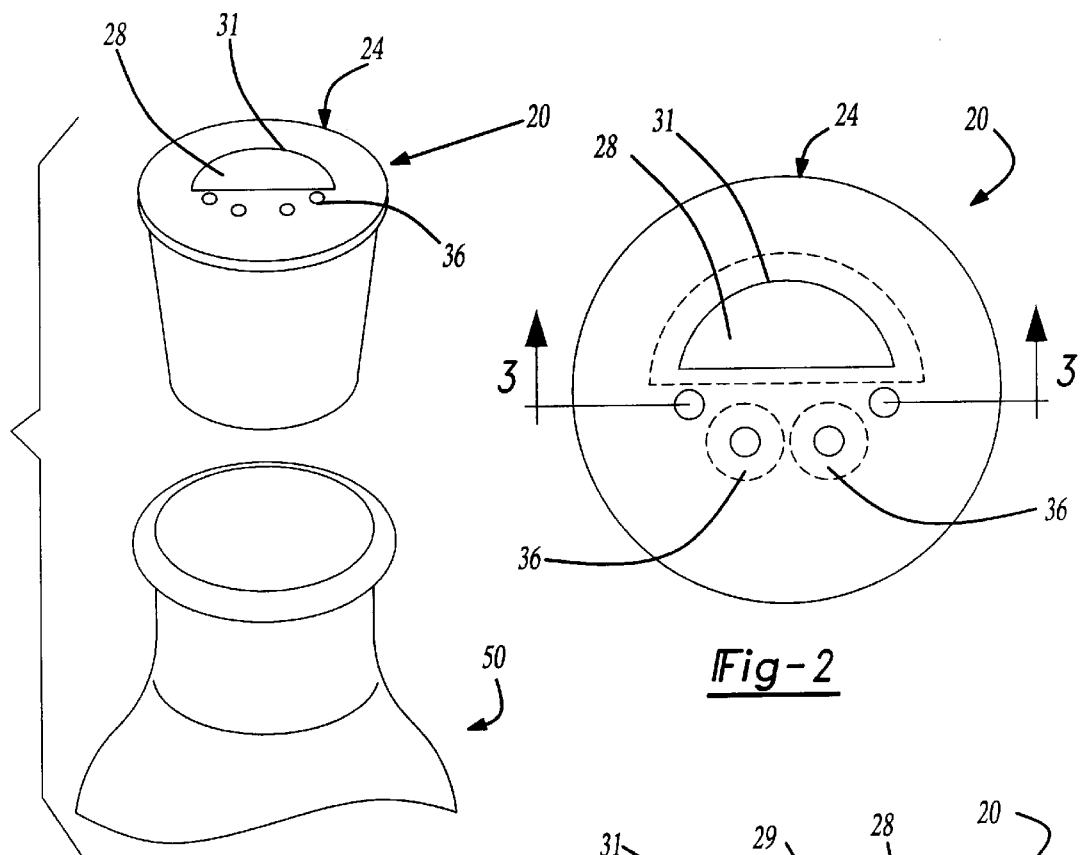
Fig-1
Fig-2
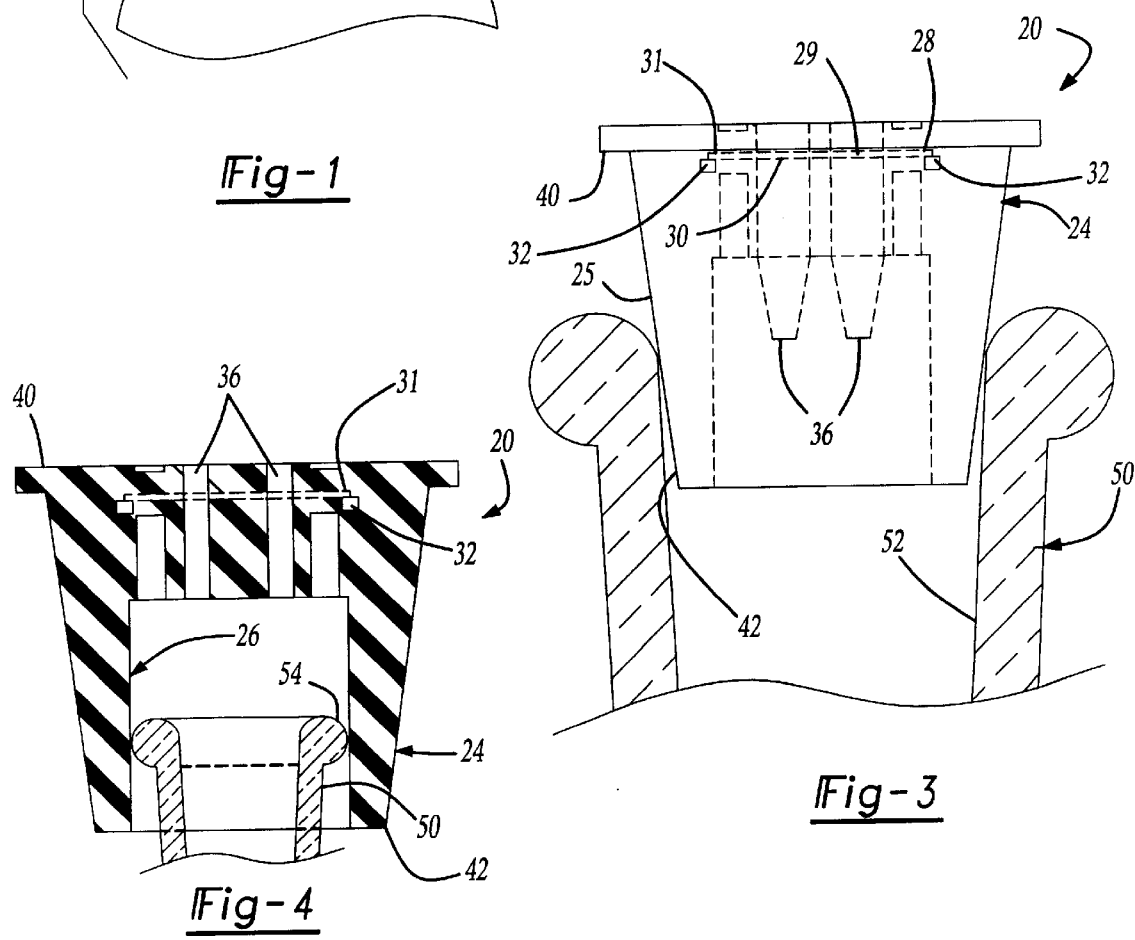
Fig-3
Fig-4

FLASK VENT AND METHOD OF MAKING SAME

CROSS REFERENCE TO RELATED APPLICATIONS

This application is a continuation-in-part of U.S. patent application Ser. No. 08/606,596, filed Feb. 26, 1996 now pending.

TECHNICAL FIELD

The present invention relates to a closure for a vessel or well. More specifically, the present invention relates to a closure for allowing sterile gas exchange therethrough.

BACKGROUND OF THE INVENTION

The use of closure devices for covering microbiological vessels, such as flasks, has been a widely accepted and longly used practice in microbiology. Closures are used in order to prevent the contamination of microorganisms being cultured or stored within the flasks by airborne contaminates or particulate matter. Additionally, these closures have been used to prevent the escape of microorganisms being cultured or stored in the flasks from being released from the flasks where they can become airborne and become contaminates themselves.

It is, generally, an absolute necessity that microorganisms or cultures must be grown under sterile conditions. Likewise, such sterile conditions must be kept in cell cultures and present day genetic manipulations of cells and cell fractions. Depending on the type of microorganism being cultured, either aerobic or anaerobic, closures have been designed to accommodate the specific growth requirements for each of these types of microorganisms. For example, aerobic microorganisms are only able to live in the presence of oxygen whereas anaerobic microorganisms are capable of growing, and in some circumstances are unable to grow, in the presence of oxygen. Therefore, for anaerobic organisms a closure may be required which is capable of maintaining sterile conditions within the interior of the flask or vessel by preventing the introduction of contaminating microorganisms while at the same time preventing the entrance of oxygen into the container or vessel. The same issues relate to such genetic manipulations as cloning and hybridization.

Another requirement for a microbiological vessel or flask closure, is that while maintaining the sterility of the microorganisms or cultures being grown therein, the closure should provide free access into the container or flask to facilitate the addition or removal of contents from the vessel or flask, such as sterile removal of microbiological culture from the vessel or flask.

Historically, cotton or gauze was formed into a plug and was inserted into the opening of a container or flask. These cotton or gauze plugs serve the general purpose of preventing contamination of the container or flask while simultaneously permitting the free exchange of oxygen with the atmosphere. This type of closure has many deficiencies such as it can be difficult to resterilize the plug for subsequent use and after repeated usage, this type of plug tends to readily decompose.

Another type of similar closure is described in U.S. Pat. No. 3,326,401 to De Long this closure is adapted to fit over the open end of a microorganism container. The closure further includes a disposable plug made from a porous material which is positioned within the closure. This device has the deficiency that it does not allow for a seal between the closure and the container or flask to be established.

Another more recent development in microbiological container or flask closures provides the advantage of a filtering device combined with a plug type closure. This closure is referred to as the Steri Plug (CTP Corp. Huntington, N.Y.). This device is constructed of multiple components including a stopper portion, a filter, and associated gaskets and retainers. Because of its complex design, this type of closure is expensive and cumbersome to use.

Additionally, a cap is described in U.S. Pat. No. 5,180,073 to Fay et al. This cap has an outer collar and an inner collar and the top portion includes a permeable section. However, this device does not disclose the use of a permeable section made from filter media nor does it disclose the method for making a cap including a sealing portion and filter media in a single step.

Therefore, it would be desirable to have a closure assembly for use with microbiological containers or flasks in which the closure assembly includes a filter membrane and a seal which allows for creating an air and fluid tight seal between the closure and the container or flask and in which the closure assembly can be produced in a one step process thereby eliminating the complexity and lowering the cost of assembly and manufacture and eliminating the deficiencies described above for prior art closure devices. It would also be advantageous to apply this technology to multiwell plates.

SUMMARY OF THE INVENTION AND ADVANTAGES

In accordance with the present invention, there is provided a closure for sealing a microorganism container which includes a resilient seal for sealing the container, a passageway extending through the seal, and a filter media extending across the passageway integrally molded to the seal for allowing sterile gas exchange therethrough.

The present invention further provides a method of making a closure by molding a seal having a passageway extending therethrough while simultaneously sealing a peripheral edge of a filter media within the passageway.

The present invention also provides a multiwell plate assembly, which includes a tray including a plurality of wells therein and a closure for sealing at least some of the wells, the closure includes a resilient framework having a plurality of sealings interconnected by the framework for sealing engagement with at least some of the wells into which the sealings are disposed, at least one of the sealings includes a passageway extending therethrough and filter media extending across the passageway for allowing sterile exchange therethrough in and out of the well in which the sealings are disposed.

The present invention provides a closure for sealing a container which includes a resilient framework including a plurality of sealings interconnected by the framework with at least one of the sealings including a passageway extending therethrough and filter media extending across the passageway for allowing sterile exchange therethrough.

The present invention further provides a plurality of plugs, each of the plugs including an opening extending therethrough defining a central axis for each of the plugs and a resilient framework interconnecting each of the plugs.

The present invention also provides a closure member which includes a plurality of wells, each of the wells including an opening extending therethrough and a framework interconnecting the wells.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a side view of a closure assembly in accordance with the present invention;

FIG. 2 is a top view of a closure assembly in accordance with the present invention;

FIG. 3 is a cross-sectional view of FIG. 2 taken along line 3—3;

FIG. 4 is a top view of a preferred embodiment of the present invention;

DETAILED DESCRIPTION OF THE INVENTION

Figure 5:
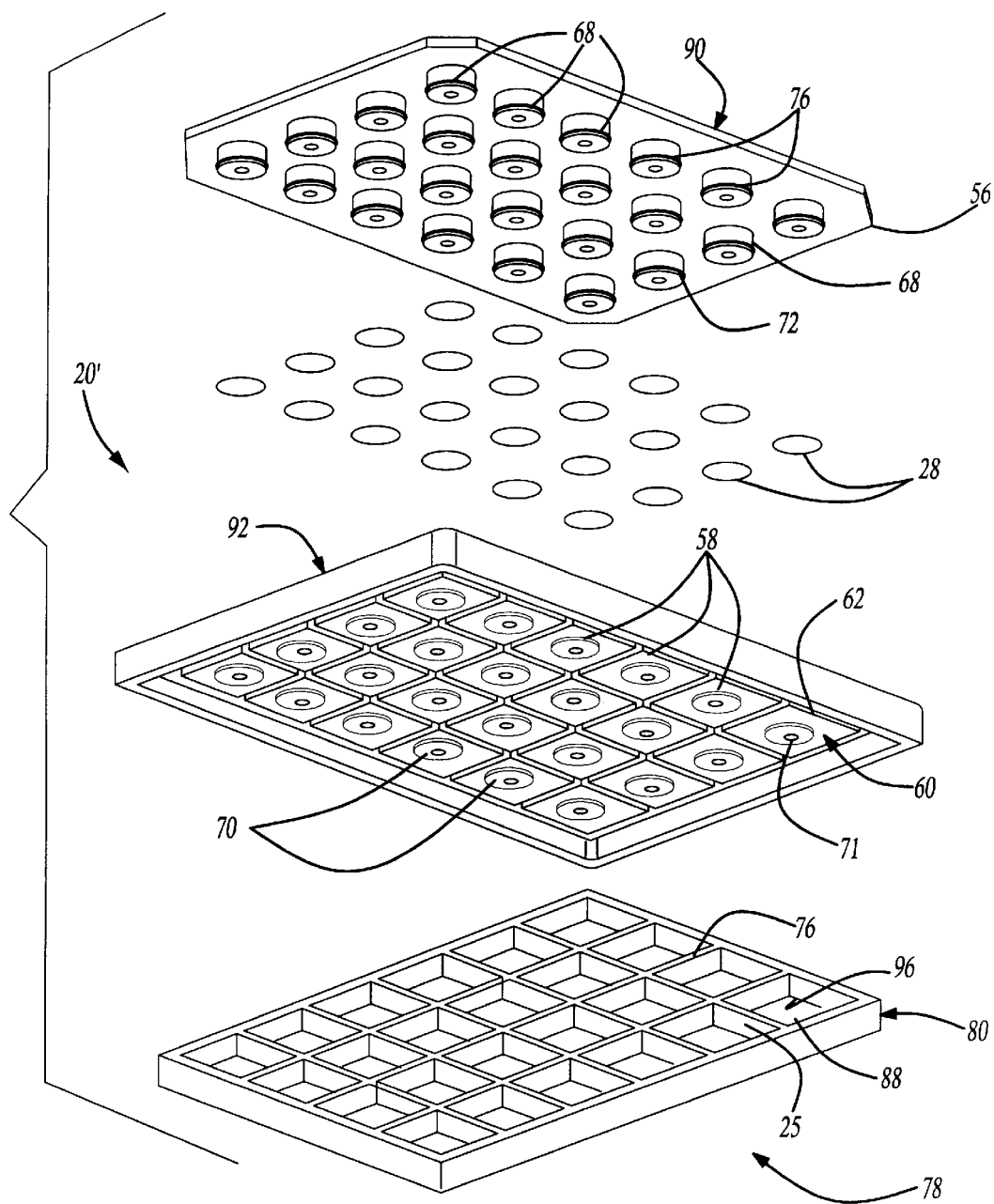
FIG. 5 is an exploded perspective view of a preferred embodiment of the present invention.

Referring to FIGS. 1 through 4, a closure assembly for sealing a microorganism container 50 is generally shown and designated by the reference numeral 20. Referring specifically to FIG. 1, the closure assembly 20 includes a resilient seal or plug 24 for sealing the closure 20 to a container 50. The closure assembly 20 further includes filter media 28 integrally disposed and connected within the seal or plug 24 for allowing sterile gas exchange therethrough.

The container 50 can be a flask, microtitre plate or other known type of container which retains liquids and microorganisms or cells, or cellular components therein for the purpose of propagating aerobic or anaerobic microorganisms or conducting other biological manipulations, such as hybridization, PCR, etc. The container 50 is preferably made of glass or pyrex®, plastic or other suitable materials which can withstand autoclaving or other such methods of sterilization.

The closure 20 can also include a port or passageway 26 axially disposed within the seal or plug 24 which extends through the seal or plug 24 allowing fluid communication between the container 50 and the external atmosphere. The passageway or port 26 is defined by a cylindrical side wall 25.

The seal or plug 24 is generally frustoconical in cross-section. The seal or plug 24 can be tapered and have a shape similar to a wedge. When an insertion end 42 of the seal or plug 24 is inserted into the container 50, the closure assembly 20 forms an air and liquid-tight seal with an inner surface 52 of the container 50. The side wall 25 of the seal or plug 24 is graduated and, therefore, it can be inserted into containers 50 having variously sized openings therein and form an air and liquid-tight seal therewith. The cross-sectional diameter of the wall 25 of the seal or plug 24 increases in the direction opposite of the insertion end 42 of the seal or plug 24 as shown in FIGS. 1 and 4. Since an infinite number of diameters can be accommodated, the closure assembly 20 can be used with and create both air and liquid-tight seals with variously sized containers 50.

The resilient seal or plug 24 is a generally unitary member formed of a resilient material which is capable of conforming and sealing to the contours of the openings of flasks or containers 50. The resilient seal or plug 24 is constructed of a material which is capable of deflecting and/or yielding to sealingly conform to or to sealingly engage with the inner surface 52 of a container such that both an air-and liquid-tight seal is formed and maintained therewith. The seal or plug 24 can be constructed or manufactured from suitable flexible and resilient materials, for example, silicones, natural synthetic rubber materials, polypropylenes, polyolefins, polyesters, polyamides, polycarbonates, polystyrenes, styrenes, co-polymers, and fluoroplastics. This list is not meant to be exhaustive and can include other suitable materials known to those skilled in the art without departing from the spirit of the present invention.

The closure assembly 20 further includes at least one filter media 28 in the form of a filter having a top surface 29, a bottom surface 30, and a peripheral edge 31. In a preferred embodiment, the filter 28 is somewhat flat or disk-shaped. The peripheral edge 31 of the filter 28 is sealed within the port or passageway 26 which axially extends through the seal or plug 24. The seal between the peripheral edge 31 and the seal or plug 24 must be both air- and liquid-tight in order to maintain the integrity and/or sterility of the closure 20 and contents of the container 50. The filter media 28 must be positioned and affixed within the port or passageway 26 such that any fluids (gaseous or liquid) can only pass through the filter media 28 and not around the periphery of the filter media 28 thereby breaching the sterility of the closure 20/container 50 system. In other words, the peripheral edge 31 of the filter media 28 must be affixed to the plug or seal 24 in such a manner to form a seal therein such that when the closure 20 is in place in the opening of the container 50, fluid and/or gas exchange can only occur across the filter media 28 thereby maintaining the sterility of the container 50 and its contents.

The filter 28 can be sealed within the passageway 26 of the seal or plug 24 by affixing or integrally molding the filter 28 within the port or passageway 26.

Referring to FIG. 4, another embodiment of the closure assembly 20 is shown. In this embodiment, the closure 20 has a generally cylindrical shape and is designed to fit over the container 50 and forms an air and liquid tight seal with an outer surface 54 of the container 50. The embodiment shown in FIG. 4 can be made in any desired size and therefore can be constructed to fit any size container 50.

Figures 6, 7:
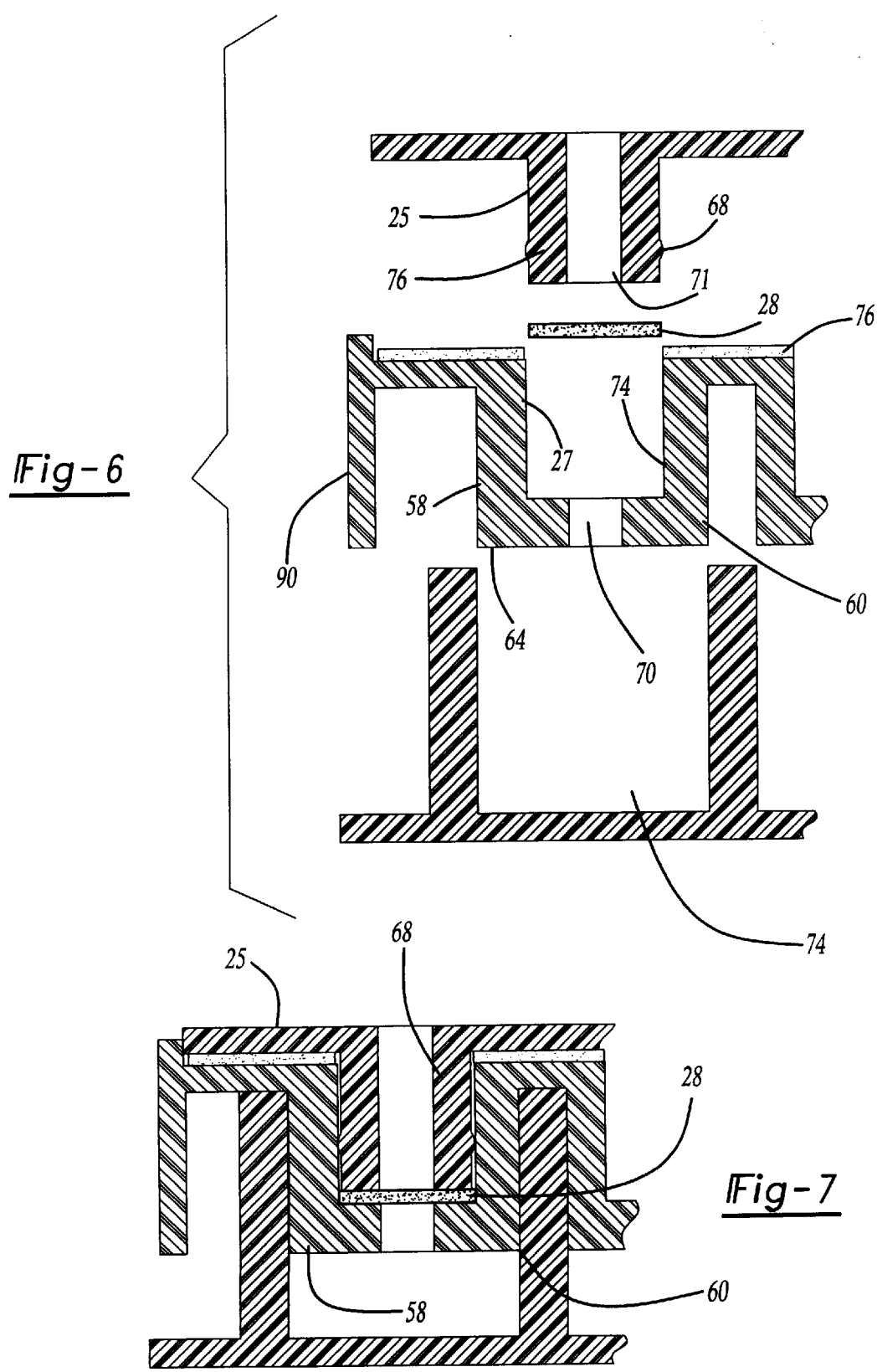
FIG. 6 is a side view in cross-section of a mold for making the present invention.
FIG. 7 is a side view in cross-section of a mold for making the present invention.

In order to provide rigidity in support to the filter 28, a support 32 can be provided adjacent to the filter. The support can be disposed about and below the peripheral edge 31 of the filter 28. The support 32 can be disposed is about the peripheral edge 31 at a position approximately level with the position of the peripheral edge 31. Referring specifically to FIG. 6, the support 32" can be disposed about and above the peripheral edge 31 of the filter 28. The support 32 can be a ring molded or affixed to either the bottom of the peripheral edge 31, the top of the peripheral edge 31, or molded or affixed to the peripheral edge 31 in the same plane as the filter 28. The support can be constructed of any suitable materials including a metal, such as stainless steel, and plastic. The material comprising the support 32 must be able to withstand the temperatures and pressures encountered during autoclaving.

Alternatively, the support can include a mesh-like matrix disposed on either the top 29 or bottom 30 of the filter 28 (not shown). The support member 32 can be constructed of any suitable material, such as the same material as comprises the closure 20.

The filter 28 and the support 32 are positioned within the port or passageway 26 of the seal or plug 24 and can be fixed in place by means such as affixation during molding of the seal or plug 24 or can be positioned and fixed in place following molding of the seal or plug 24 such as by gluing or embedding the filter 28 and support 32, in the plug or seal 24 to the seal closure 20.

A skirt 90 can be added around the outer perimeter at the support 32, as an additional measure to ensure proper seal closure.

The filter 28 and the support 32 can be affixed to one another by means including molding or other types of affixation such as gluing, cementing ultrasonics, insert molding, heat sealing or UV curing.

The filter media 28 can include any suitable materials or membranes such as depth media including HEPA or OPA rated glass microfiber, cotton wool, a steel plug, hydrophobic membranes such as polypropylenes, polytetrafluoroethylenes (PTFE), polysulfones, polyvinyldifluoride (PVOF), or any other porous material. Further, the filter material may be woven or nonwoven and may contain multiple layers. These multiple layers may be made up of the same or different filter media 28. This list of materials is not intended to be exhaustive and other suitable materials known to these skilled in the art can be utilized without departing from the spirit of the present invention. The filter media 28 is made from a material which is capable of permitting the exchange of gas thereacross, but will not permit the passage of micro-organic contaminants.

The closure assembly 20 can include at least one aperture or opening 36 extending therethrough to allow for the insertion of tubing, thermometer or the like therein. Since the aperture 36 is disposed within the seal or plug 24, the aperture 36 is able to conform and perfect a seal about any tubing or the like placed therein. The aperture 36 allows for sterile access to the interior of the container 50 and the contents therein without the risk of introducing any contamination.

The present invention can be adapted to be an effective sealing device for a multiwell tray system. As shown specifically in FIG. 5, the closure assembly 20' can include a resilient framework 56 which contains therein a plurality of sealings 58 which are interconnected by the framework 56. This resilient framework 56 can be constructed of any suitable materials including metal, such as stainless steel and plastic. However, this list is not meant to be exhaustive and can include other suitable materials known to those skilled in the art without departing from the spirit of the present invention.

As shown in FIGS. 6 and 7, the assembly can be a three part system. The system includes an upper member 90 and lower member 92. The sealings or plugs 58 are made up of a female portion 60 of the lower member 92 having at least one opening 70 extending therethrough and a male portion 68 also having an opening 71 extending therethrough. The male portion 68 of the upper member 90 is made such that it is disposed within the female portion 60 and the openings 70, 71 are properly aligned. Fitted between the female portion 60 and the male portion 68 is a filter media 28 which extends between the openings 70, 71. The filter media 28 is made from a material which is capable of permitting the exchange of gas thereacross, but will not permit the passage of microorganic contaminants, such media having been discussed above.

The upper member 90 and the lower member 92 portions can be connected by any bonding technique which is capable of holding the two parts together, for example, glue, heat welding, suction force, ultrasonics or injection molding.

More specifically, the male portions 68 define the plugs which each have a wall 25 extending from the resilient framework 56 thus interconnecting the plugs 24. Each of these plugs 24 have a base portion 72 which includes at least one opening 71. Additionally, each of the female portions 60 defines well 74 having side walls 27 and a bottom base portion 64 which includes an opening 70. Each of the walls 25 of the plug 24 fit in sealing engagement with the side walls 27 of the well 74.

Each of the side walls 25 of the plugs 24 also includes a shoulder 76 extending outwardly therefrom thus forming a sealing shoulder 76 about said wall portion 25, forming a perfect seal against the side walls 27 of the well 74. The shoulder 76 acts as a sealing ring to engage the well and further perfect a seal therewith. This sealing engagement forms a liquid tight seal which is maintained therewith.

The seal or plug 24 can be constructed or manufactured from suitable, flexible and resilient materials, for example, silicones, natural or synthetic rubber materials, polyolefins, and fluoroplastics. This list is not meant to be exhaustive and can include other suitable materials known to those skilled in the art.

Referring specifically to FIG. 5, the multiwell plate assembly can include a tray 80 including a plurality of wells 96 therein. The closure assembly 20' includes the resilient framework 56 which has therein the plurality of sealings 58 which are interconnected by the framework 56. The sealings 58 can be forced to sealing engagement with at least some of the wells 74 into which the sealings 58 are disposed. At least one of the sealings 58 includes a passageway 86 extending therethrough. Additionally, filter media 28 extends across the passageway 86 for allowing sterile exchange of gas therethrough in and out of the well 74 upon which the sealing 58 is disposed.

Figure 8:
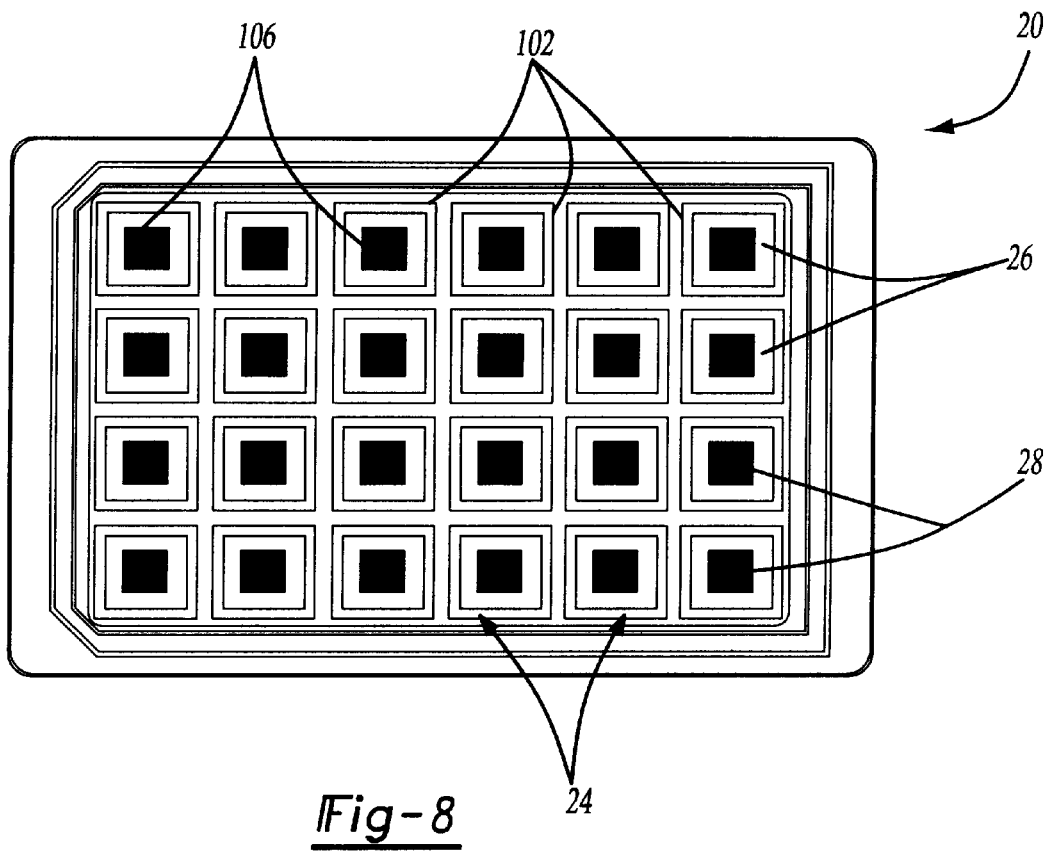
FIG. 8 is a top view of a further embodiment of the present invention.
Figure 9:
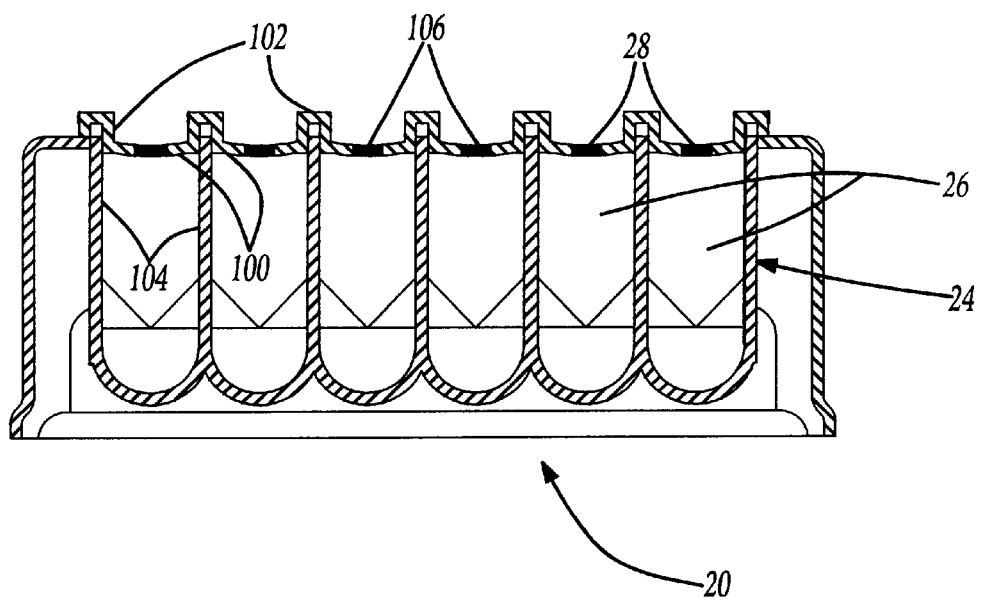
FIG. 9 is a side view of the further embodiment of the present invention.

Additionally, as shown in FIGS. 8 and 9, the closure assembly 20 can be a multiwell assembly made of a single piece of material. Preferably, the assembly 20 is injection molded with the filter media 28 placed within the assembly 20 such that the peripheral edge 31 of the filter 28 is sealed within the passageway 26 in the seal plug 24 while the closure assembly 20 is being formed.

As shown in FIGS. 8 and 9, the assembly can be formed into a single piece including plug sections 100 surrounded by gripping portions 102. The gripping portions sealingly engage the upper portion of walls 104 of the tray wells. Media 106 is integrally connected to the framework of the plug sections.

The present invention further provides a method of making a flask closure 20 by molding the seal or plug 24 having the port or passageway 26 extending therethrough while simultaneously sealing the peripheral edge 31 of the filter media 28 within the port or passageway 26. That is, a one-piece, unitary closure assembly 20 is formed while simultaneously sealing the peripheral edge 31 of the filter 28 within the passageway 26 of the seal or plug 24. The molding step is accomplished by techniques well known to those skilled in the art.

The present invention can be practiced with various shaped filter medias 28 as shown in FIG. 1 and FIG. 4 as long as the filter media 28 can be supported and the peripheral edge 31 of the filter media 28 is available for sealing affixation to the passageway 26 of the sealer plug 24. Additionally, the present invention can be practiced with multiple layers of filter media 28. These layers may be made up of layers of the same or different filter media 28. Also, a single sheet of filter media 28 may be utilized for the entire assembly 20 by placing the filter media 28 inside the assembly 20 prior to an injection molding procedure.

The method of forming the closure assembly 20 can also include the step of disposing the support 32 within the passageway 26 either during the molding step or following the molding step. The method generally includes sizing the filter media 28 to a desired size. The support 32 can also be specifically dimensioned. The filter media 28 and the support 32 can be loaded into a mold cavity and are held in place on top of core pins by locator pins. A suitable material, such as silicone, can then be injected into the mold cavity. The silicone fills the mold cavity and encapsulates the filter media 28 and support 32 and can then be cured by means such as utilizing heat from the mold. After a suitable curing period, the closure assembly 20 can be removed from the mold.

In another method embodiment of the present invention as shown in FIGS. 8 and 9, the closure assembly 20 is made by gluing or otherwise affixing a die cut filter 28 onto the support. Specifically, an activator, such as Loctite 770, is applied to the top surface at the support 32. This is allowed to dry for approximately three minutes or time as required for the activator. A bead of adhesive, such as Loctite 454, is then applied to the same surface onto which the filter media 28 is immediately pressed. After the adhesive has dried, the assembly 20 is ready for usage.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

What is claimed is:

1. A closure (20) for sealing a micro-organism container (50), said closure (20) comprising:

resilient sealing means (24) for sealing the container (50);

a passageway (26) extending through said sealing means (24); and at least one filter media extending across said passageway (26) integrally molded of material different from that of said resilient sealing means to said sealing means (24) for allowing sterile gas exchange therethrough, said closure including a resilient framework including a plurality of said sealing means interconnected by said framework, each of said sealing means including a female portion having at least one opening extending therethrough and a male portion including an opening extending therethrough, said male portion being disposed within said female portion whereby said openings are aligned, said filter media being contained between said male and female portions and extending between said opening.

2. A closure (20) as set forth in claim 1, wherein said sealing means (24) is a unitary member having a port (26) extending therethrough and said filter media (28) integrally molded within said port (26).

3. A closure (20) as set forth in claim 1, wherein said sealing means (24) includes at least one aperture (36) extending therethrough to allow insertion of tubing therein.

4. A closure (20) as set forth in claim 1, wherein said resilient sealing means (24) has a frustoconical cross section.

5. A closure (20) as set forth in claim 1 wherein each of said male portions define plugs having a wall extending from a framework interconnecting said plugs, each of said plugs having a base portion including at least one of said openings, each of said female portions defining a well having side walls and a bottom base portion including one of said openings, each of said walls of said plugs fitting in sealing engagement with said side wells of said wells.

6. A closure (20) as set forth in claim 5 wherein each of said side walls of said plugs include a shoulder extending outwardly therefrom forming a sealing shoulder completely about said wall portion thereof for perfecting a seal against said side wells of said well.

7. A closure (20) as set forth in claim 1, wherein said filter media includes a filter membrane (28).

8. A closure (20) as set forth in claim 7, wherein said filter membrane (28) is constructed of a hydrophobic material.

9. A closure (20) as set forth in claim 7, wherein said filter membrane (28) includes at least one support means (32,32', 32",32''') disposed adjacent to said filter membrane (28) for supporting said filter membrane (28).

\* \* \* \* \*